United States Patent
Kuenzli et al.

(10) Patent No.: US 7,509,874 B2
(45) Date of Patent: Mar. 31, 2009

(54) APPARATUS FOR THE TESTING OF ELASTIC TEXTILE LEG GARMENTS

(75) Inventors: Daniel Kuenzli, Teufen (CH); Walter Braun, St. Gallenkappel (CH); Muck Ruettiger, Iffezheim (DE)

(73) Assignee: Salzmann AG, St. Gallen (CH)

( * ) Notice: Subject to any disclaimer, the term of this patent is extended or adjusted under 35 U.S.C. 154(b) by 76 days.

(21) Appl. No.: 11/374,428

(22) Filed: Mar. 14, 2006

(65) Prior Publication Data
US 2007/0012120 A1    Jan. 18, 2007

(30) Foreign Application Priority Data
Mar. 14, 2005   (CH) ..................... 0432/05
Nov. 14, 2005   (CH) ..................... 1813/05

(51) Int. Cl.
*G01N 3/08* (2006.01)
(52) U.S. Cl. ............... 73/826; 73/159; 73/788; 73/790; 73/794; 73/796; 73/831; 73/832; 73/855; 73/862.391; 73/862.42; 223/75; 223/77
(58) Field of Classification Search .......... 73/159, 73/788, 790, 794, 796, 831, 826, 832, 855, 73/862.391, 862.42; 223/75, 77
See application file for complete search history.

(56) References Cited

U.S. PATENT DOCUMENTS

| | | | | |
|---|---|---|---|---|
| 2,369,661 A | * | 2/1945 | Dangelmajer ............... 73/159 |
| 2,661,877 A | * | 12/1953 | Albertson et al. ........... 223/75 |
| 2,675,703 A | * | 4/1954 | Hemmerich et al. .......... 73/159 |
| 3,503,257 A | * | 3/1970 | McElhaney et al. ..... 73/862.041 |
| 3,750,291 A | * | 8/1973 | Foreman ...................... 33/2 A |
| 4,137,763 A | * | 2/1979 | Swallow ...................... 73/159 |
| 4,417,401 A | * | 11/1983 | Aisaka et al. ................. 33/512 |
| 4,491,255 A | * | 1/1985 | LaChapelle .................. 223/37 |
| 6,334,363 B1 | * | 1/2002 | Testud et al. ........... 73/862.046 |
| 6,499,356 B1 | * | 12/2002 | Flaud et al. ................... 73/831 |

* cited by examiner

*Primary Examiner*—Harshad Patel
*Assistant Examiner*—Freddie Kirkland, III
(74) *Attorney, Agent, or Firm*—Moetteli & Associés SàRL

(57) ABSTRACT

The apparatus has an elongate and vertically running carrier (90) for pressure sensors (50), which precedes a group of levers (71). The cross section of this carrier (90) is arcuate, so that it has two flanks (93, 94). During the testing of a leg garment (80), this carrier (90) simulates the region of the shin. The apparatus has, furthermore, moldings or stays (88) which are carried by the levers and which simulate the rear face of the calf or of the thigh of a leg. The width of these stays corresponds to the width of the calf or of the thigh of a leg. The apparatus also comprises two longitudinally running groups (50) of pressure sensors, one of which is in each case assigned to outside of one of the flanks (93, 94) of the carrier (90). The leg garment (80) to be tested, in order to test it, is slipped over this apparatus in such a way that it lies on the outer faces both of the carrier (90) and of the stays and exerts pressure on the pressure sensors (51). Free-standing portions (81, 82) of the leg garment (80) extend between the carrier (90 ) and the stay (88). An evaluation device is provided, which can evaluate and indicate the values emitted by the pressure sensors.

8 Claims, 6 Drawing Sheets

APPARATUS FOR THE TESTING OF ELASTIC TEXTILE LEG GARMENTS

The present invention relates to an apparatus for the testing of elastic textile leg garments, in particular of stockings or tights, medical compression stockings and support stockings.

Elastic textile leg garments must be shaped such that they follow as exactly as possible the contour of the leg of the person wearing the leg garment. This is because it is only in such a case that the leg garment can fully exercise its function, without there being locations along the leg at which the leg garment exerts too high or too low a pressure. In order to achieve this, it is known first to measure the leg of the wearer of the leg garment. This measurement is carried out in that the circumference of the leg is measured at specific locations on the leg. During this measurement, for example the circumference of the leg is measured in the region of the ankle, at the start, in the middle and at the upper end of the calf, in the knee region and in the region of the thigh, to be precise in the middle and at the upper end of the latter. Where tights are concerned, the circumference is also measured in the region of the buttock, and, if appropriate, also in the region of the waist. The leg garment is then manufactured on the basis of these stipulations. Afterwards, however, it is also necessary to determine whether the stipulations have been adhered to in the manufactured product.

Apparatuses for the measurement of finished stockings are already known. In one of these apparatuses, the longitudinal edges of the laid-flat stocking which lie opposite one another are slipped onto needles which form two rows along the stocking length. These needles are mounted moveably, specifically in such a way that the distance between two needles lying opposite one another in the needle rows can be changed. The measurement as to whether the stipulations have been adhered to during the manufacture of the stocking may take place, for example, in that needles lying opposite one another are brought to distances from one another which correspond to the stipulations, and in that the tension in the stocking between two needles lying opposite one another is measured. Admittedly, it is thus possible to ascertain whether the contour of the stocking has the profile defined by the stipulations. However, because it is pinned onto the needles, the measured stocking becomes unsaleable. When it is remembered that such stockings are often single products, the measurement of the finished stockings with the aid of the apparatus just mentioned is ineffective.

The object of the present invention is to eliminate said and also further disadvantages of the prior art.

As regards the apparatus of the generic type initially mentioned, this object is achieved, in a way defined in the defining part of patent claim 1.

Figure 1:
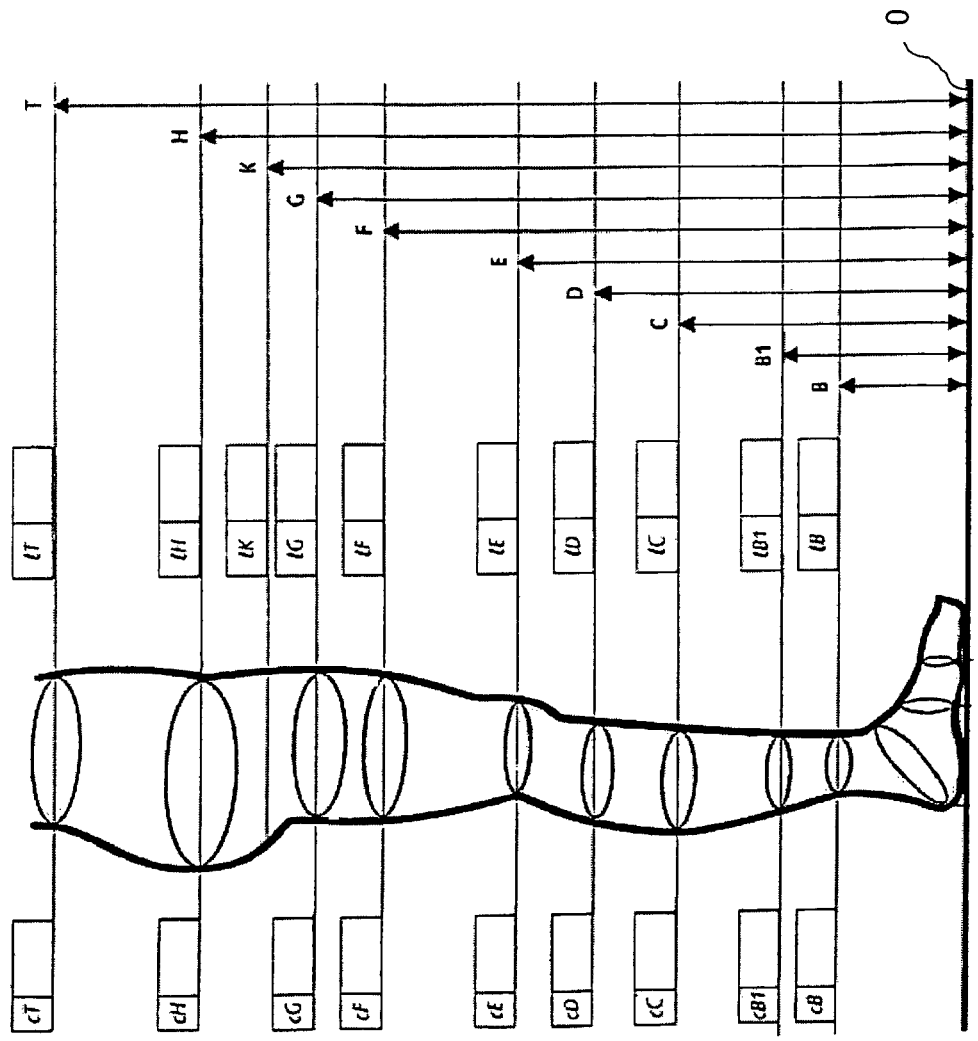
Figure 2:
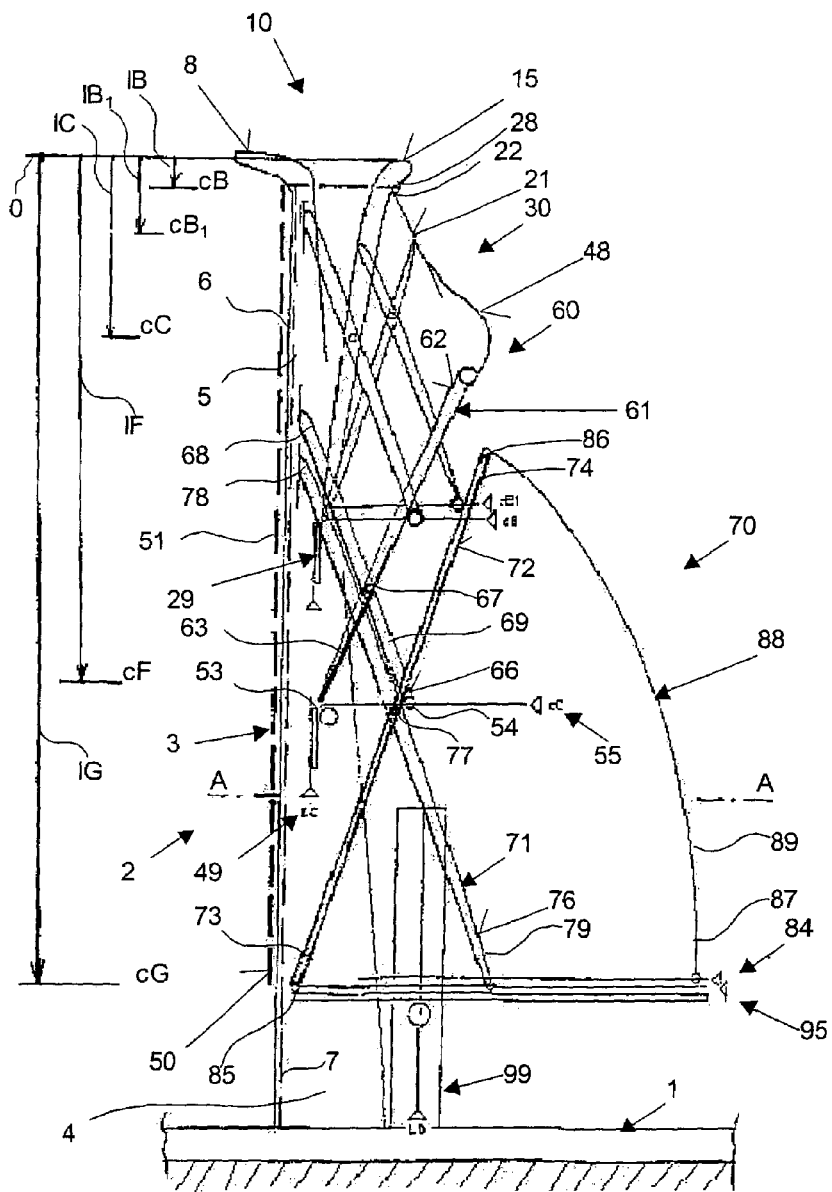
Figure 3:
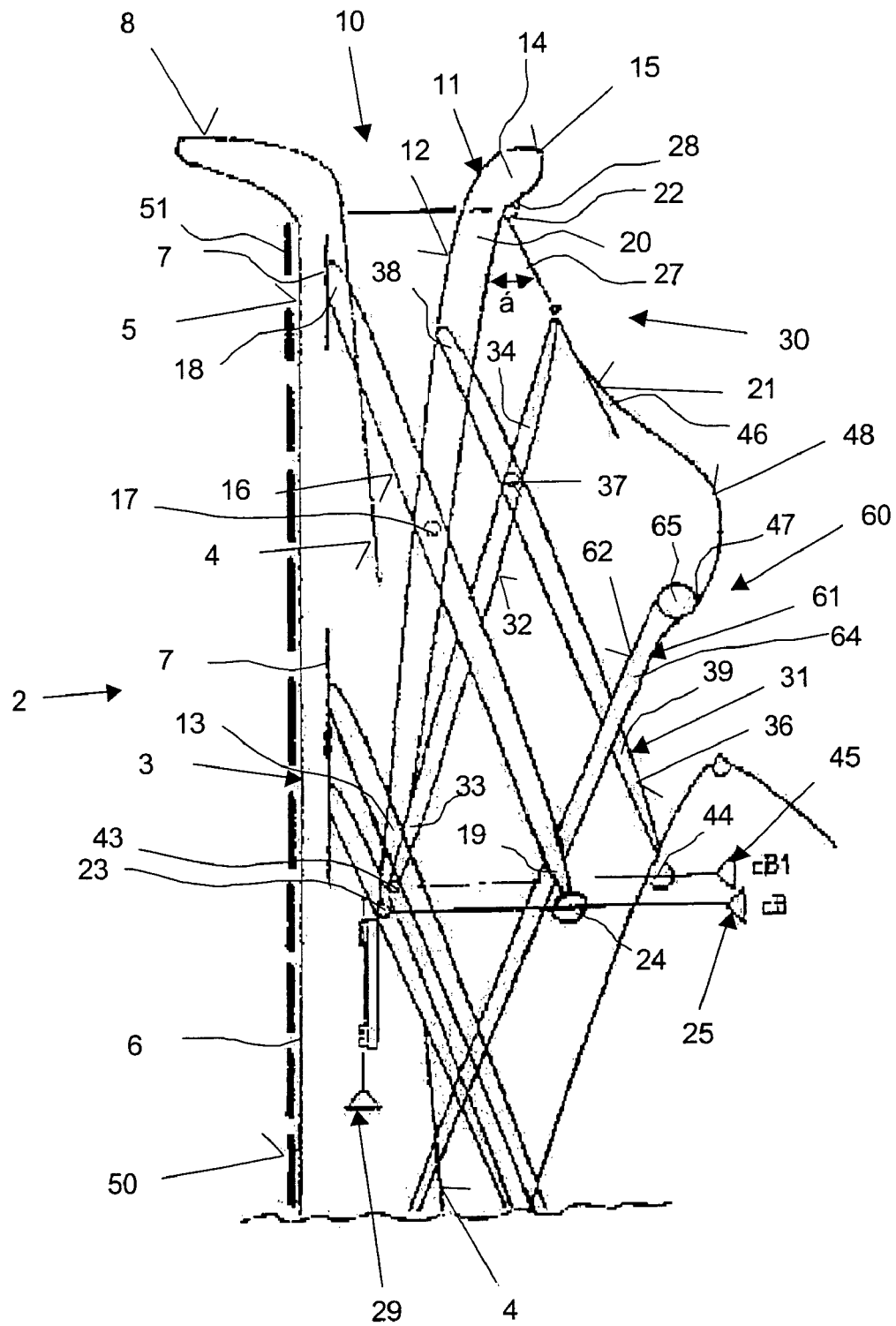
Figure 4:
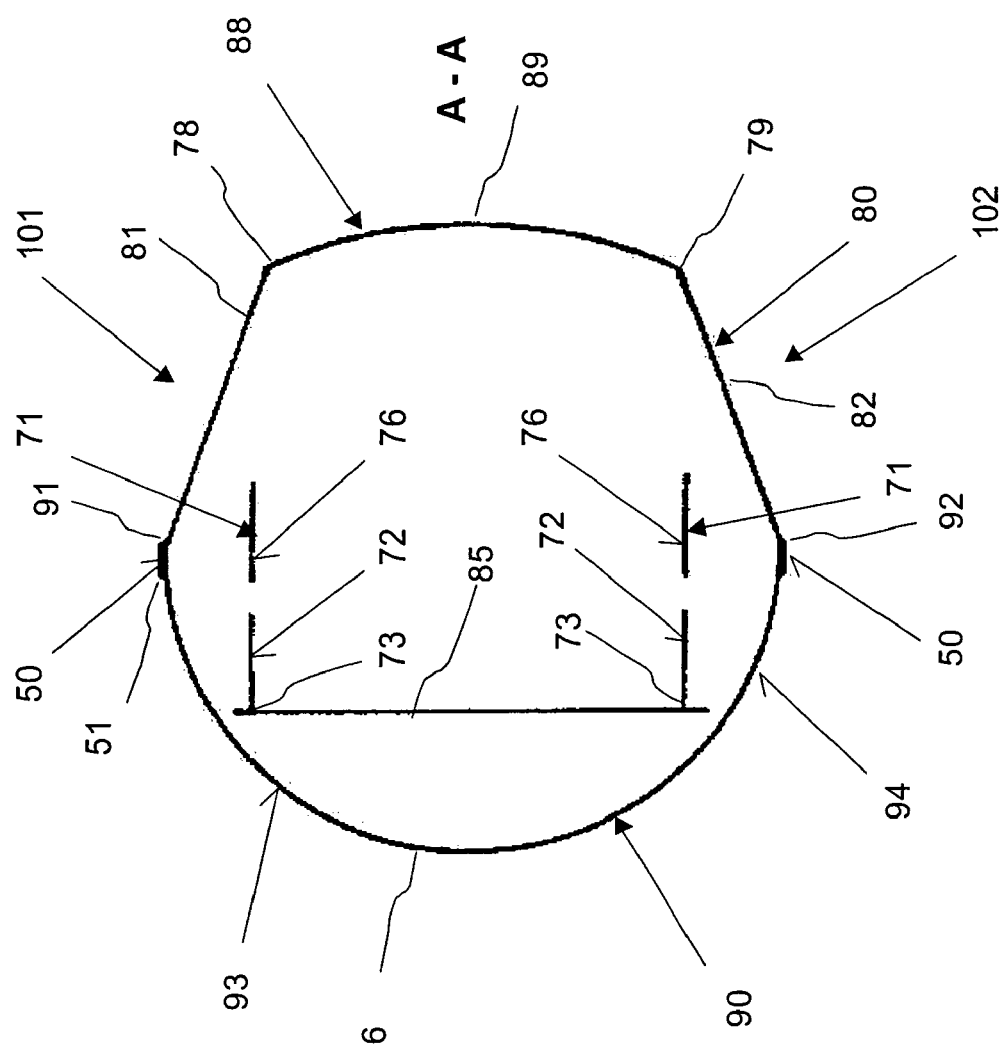
Figure 5:
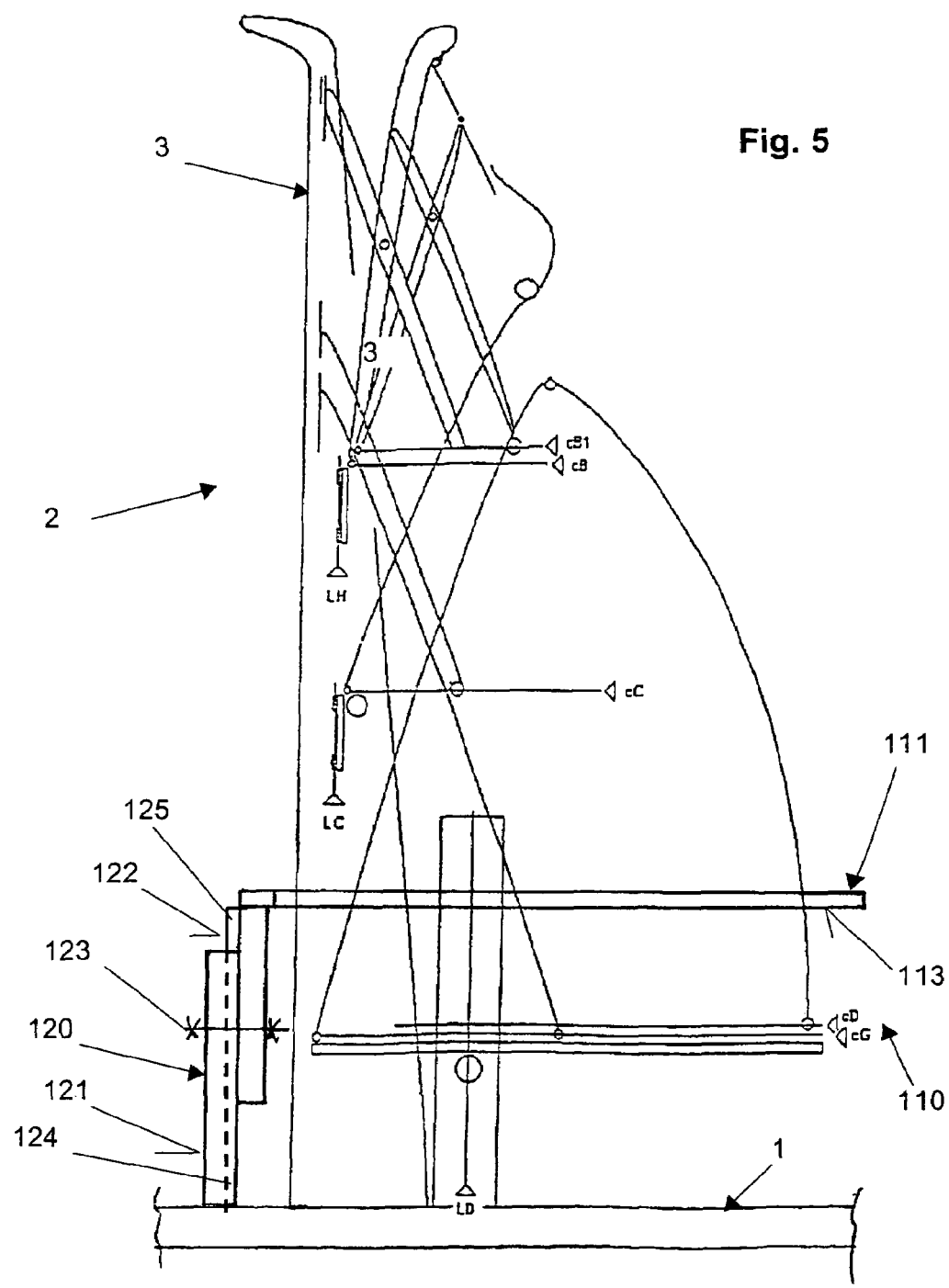
Figure 6:
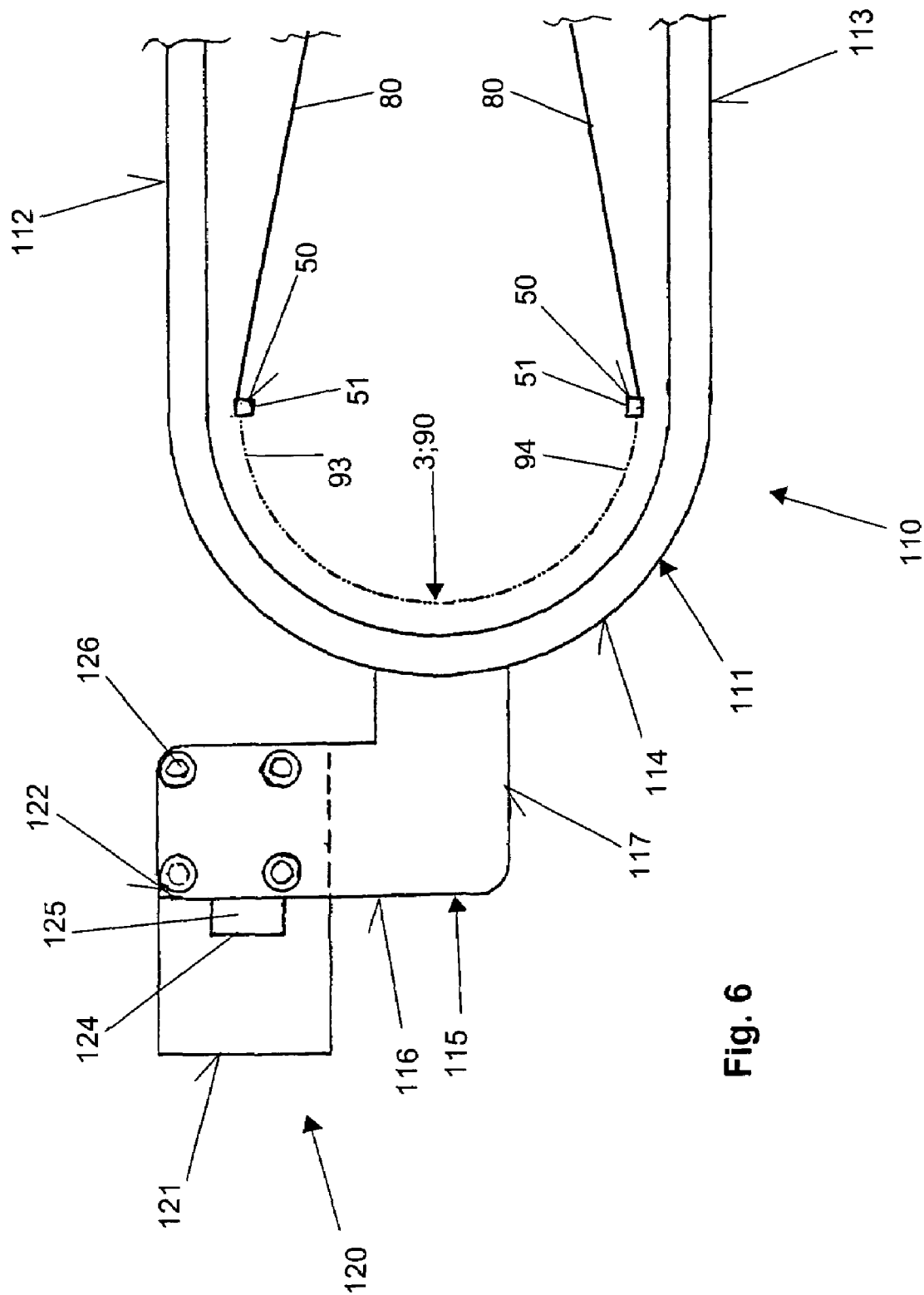

Embodiments of the present invention are explained in more detail below with reference to the accompanying drawings in which:

FIG. 1 shows a model of a human leg where it can be demonstrated at which locations on the leg circumferential measurements can be carried out, FIG. 2 shows a side view of a first embodiment of the present apparatus which is illustrated for the most part with the aid of a kinematic diagram, FIG. 3 shows, enlarged, a detail from FIG. 2, FIG. 4 shows a merely diagrammatic horizontal section A-A through a further version of the present invention which corresponds to the apparatus according to FIG. 2, FIG. 5 shows yet another embodiment of the present invention, the illustration of which corresponds largely to the illustration in FIG. 2, and FIG. 6 shows a top view of the embodiment of the present apparatus, as illustrated in FIG. 5.

FIG. 1 shows a model of a human leg where it can be demonstrated at which locations or in which regions of the human body circumferential measurements can be carried out, so that the leg garments, such as, for example, medical stockings or tights, can be manufactured. The foot of the leg garment could, in principle, also be measured. For the purposes of the present instance, measurements only above the foot are taken into account here. During such a measurement, for example, the circumference of the leg is measured in the region of the ankle cB, at the start cB1 of the calf, in the middle cC of the calf and at the upper end cD of the calf, in the knee region cE in the middle cF of the thigh and at the upper end cG of the latter. Where the manufacture of tights is concerned, the circumference cH in the region of the buttocks and the circumference cT of the waist are then also measured.

Human legs differ from one another not only in the size of the circumference in said regions of the latter, but also in the distances between these regions. The distance differences are due to the different lengths of the legs. These lengths, too, are therefore determined during the measurements of a leg. These lengths are expediently related to the foot underside, in particular to the underside of the heel. The region of the ankle cB is located at the distance LB from the heel, and so on and so forth, as indicated on the right in FIG. 1.

The present apparatus for the nondestructive testing of elastic textile leg garments, such as, for example, of stockings, tights, etc., is designed in such a way that it makes it possible to set the circumferential values measured in the respective regions of a leg in the corresponding regions of the apparatus. Furthermore, the present apparatus makes it possible to measure the amount of tension prevailing in those regions of the leg garment which correspond to said regions of the leg. This ensures not only that the finished product exercises its health-promoting action, but that the leg garment can also be worn comfortably.

FIG. 2 shows a side view of one of the embodiments of the present apparatus. FIG. 3 shows an enlarged detail from the upper region of FIG. 2. The present apparatus is illustrated for the most part by means of what is known as a kinematic diagram. This diagram also shows, inter alia, the principle of the present apparatus for a specific region of the leg. This principle can then be applied repeatedly in an apparatus of this type in order to test a plurality of regions of a leg garment.

The present apparatus has a baseplate 1, on which a main support 2 of the present apparatus is located. This main support 2 has an elongate basic body 3 which is designed essentially as a hollow rail. This rail 3 has an approximately U-shaped cross section in the instance illustrated in FIGS. 2 and 3. However, this rail 3 may also have an L-shaped or even a square cross section. The main support 2 inserted in the baseplate 1 is not a mandatory component of the present apparatus. What is important, above all, is the rail 3 to which the remaining components of the present apparatus are assigned. FIGS. 2 and 3 illustrate only the front leg 4 of the rail 3 having the U-shaped cross section. This front U-leg 4 is connected via a connecting web 5 to the second U-leg which lies behind the front U-leg 4 and which is therefore concealed by the latter. At least the outer face 6 of the connecting web 5 is rounded. It may be expedient for the inner face 7 of the connecting web 5 also to have a concave design according to the rounded outer face 6 of the latter.

The upper end part of the main support 2 or of the rail 3 has a laterally bent portion 8. This rail portion 8 is bent such that it lies above the connecting web 5 of the rail 3 and extends upward obliquely with respect to the longitudinal direction of this rail 3. This essentially hook-shaped portion 8 of the main support 2 simulates the region of the tip of a foot. In a further embodiment of the present apparatus, the region of the foot tip 8 may also be designed as a portion of a hollow molding running obliquely upward and consisting, for example, of a plastic. This molding precedes the remaining components of this apparatus which are described below. The cross section of this molding may run arcuately, specifically, for example, such as is stated above with regard to the cross section of the main support 2.

The present apparatus comprises, furthermore, measuring devices 10. The respective measuring device 10 comprises a lever mechanism and at least one pressure sensor 51. The components of the respective measuring device 10 which participate actively in the measurement are located in each case at that level L of a leg garment where pressure measurements are to be carried out. For this purpose at least the active faces of the pressure sensors 51 are attached to the outer face 6 of the rail 3. The rail 3 may therefore also be referred to as a carrier of the pressure sensors 51. The pressure sensors 51 are combined into at least one vertically running sensor device 50, the pressure sensors 51 forming a row within a sensor device 50. In the instance illustrated in FIGS. 2 and 3, the sensor device 50 is located forward in the middle of the front face 5 of the carrier 3. It is more expedient, however, if there are two sensor devices 50, each of which is assigned respectively to one of the flanks or to the one of the legs 4 of the carrier 3. The active faces of the pressure sensors 51 of the sensor devices 50 are located on the outer face of the legs 4 of the carrier 3. Each of the pressure sensors 51 is electrically connected individually to a central evaluation unit (not illustrated).

In the upper region of FIG. 2, inter alia, a first of said measuring devices 10 is also illustrated, which is intended and designed for measuring the pressure in the region cB of the ankle. This region of the present apparatus is illustrated, enlarged, in FIG. 3. The measuring device 10 also comprises, inter alia, a lever mechanism 11 (FIG. 3) which has a first lever 12. This lever 12 extends essentially vertically. In the example illustrated, the lower end 13 of this first lever 12 is mounted pivotably on the main support 2 below the bend 8 by means of an axle 23. Expediently, this lower end 13 of the first lever 12 is mounted pivotably on the U-leg 4 of the support basic body 3, said U-leg lying in the foreground in FIGS. 2 and 3. The upper end 14 of the first lever 12 is located approximately level with the hook-shaped spur 8 of the support basic body 3. The upper end 14 of the first lever 12 likewise has a laterally bent spur 15 which, however, is bent such that it points in a direction opposite to the direction of the bend 8 on the support basic body 3. The spur or bend 15 at the upper end 14 of the first lever 12 simulates the heel of a foot or of a leg garment.

The lever mechanism 11 has, furthermore, a second lever 16 which likewise extends essentially vertically. This second lever 16 crosses the first lever 12. These levers 12 and 13 are connected pivotably to one another in the region of their crossing point with the aid of an axle 17. These levers 12 and 16 thus assigned to one another form what is known as a scissor mechanism. In the instance illustrated, said axle 17 lies approximately in the middle of the length of said levers 12 and 16. The upper end 18 of the second lever 16 of this scissor mechanism 11 lies on the inner face 7 of the support basic body 3 in the example illustrated.

The lower end 19 of the second lever 16 is connected to the spindle nut 24 of a spindle drive 25 for the value cB. This spindle drive 25 is oriented horizontally and is attached to the support basic body 3 approximately where the lower end 13 of the first lever 12 is mounted pivotably. The spindle drive 25 is arranged and designed such that it can move the lower ends 13 and 19 of the levers 12 and 16 of the scissor mechanism 11 toward one another and away from one another. The distance between the bends 8 and 15 at the upper ends of these levers 12 and 16 is reduced or increased correspondingly.

A rod 21 is attached pivotably at one end to the upper leg 20 of the first lever 12 by means of a joint 22. This joint 22 is located below the bend 15 of the first lever 12, so that this joint 22 lies on the side, facing away from the pressure sensors 51, of that leg 20 of the first lever 12 that lies above the pivot axle 17. The joint 22 is located at a distance 28 below the bend 15 at the upper end 14 of the first lever 12. Within this portion 28 of the lever 12 which extends between the bend 15 and the joint 22 lies that level of the present apparatus where the measurement of the value cB is carried out, specifically with the aid of the uppermost pressure sensor 51. Since said portion 28 constitutes a fixed component of the first lever 12, the distance between the sensor 51 and that face 28 on the lever 12 which faces away from the latter can likewise be adjusted with the aid of said first spindle drive 25.

So that the position of the heel 15 and therefore also the measurement level cB can be changed in a vertical direction, with the result that the length of the leg can be taken into account during the manufacture of the leg garment, the pivot bearing 23 at the lower end 13 of the first lever 12 is fastened to the spindle nut of a vertically oriented and fixedly mounted spindle drive 29.

Furthermore, in the upper region of FIG. 2, active parts of a second measuring device 30 which is intended and designed for measuring the pressure in the region cB1 at the start of the calf are illustrated. This measuring device 30 also comprises, inter alia, a lever mechanism 31 which has a first lever 32. This lever 32 extends essentially vertically. The lower end 33 of this first lever 32 is mounted pivotably. Expediently, this end 13 of the first lever 32 is mounted pivotably by means of a shaft 43 on a U-leg 4 of the support basic body 3, said U-leg lying at the front in FIGS. 2 and 3. The upper end 34 of the first lever 32 is located at a distance below the bend 15 on the first lever 12 and is assigned to the rod 27. In this rod 27, a slot (not illustrated) is formed, which extends between the ends of this rod. This slot commences and terminates at a distance from the ends of this rod 21. The upper end 34 of the first lever 32 of the second measuring device 30 is mounted longitudinally displaceably in this slot.

The second lever mechanism 31 has, furthermore, a second lever 36 which likewise extends essentially vertically. This second lever 36 crosses the first lever 32. These levers 32 and 36 are connected pivotably to one another in the region of their crossing point with the aid of an axis 37. These levers 32 and 36 thus assigned to one another consequently form a second scissor mechanism. In the instance illustrated, said axis 37 lies above the middle of the length of said levers 32 and 36. The upper end 38 of the second lever 36 of this scissor mechanism 31 is supported on the upper leg 20 of the first lever 12 of the first scissor mechanism 11 in the instance illustrated. Under some circumstances, it would be possible for the upper end 38 of the second lever 36 of this second scissor mechanism 31 to lie on the inner face 7 of the support basic body 3.

The lower end 39 of the second lever 36 is connected to the spindle nut 44 of a second spindle drive 45 for the value cB1. This spindle drive 45 is oriented horizontally and is attached approximately where the lower end 33 of the first lever 32 is mounted pivotably by means of the shaft 43. The spindle drive 45 is arranged and designed such that it can move the lower ends 33 and 39 of the levers 32 and 36 of the second scissor mechanism 31 toward one another and away from one another.

The distance between the upper ends 34 and 38 of the levers 32 and 36 is correspondingly reduced or increased. When the distance between the upper ends 34 and 38 of the levers 32 and 36 is changed, the upper end 34 of the first lever 32 moves to the right. Since this end 34 of the first lever 32 is mounted in the rod 21, an angle alpha, which extends between the upper leg 20 of the first lever 12 and the rod 21, is in this case increased. As a result, the distance between the rear side of the rod 21 and the pressure sensor 51 lying at the same level also changes. In this way, different sizes of the circumference of the leg can be set in the region cB1 at the start of the calf.

So that the position of the measurement region cB1 can be changed in the vertical direction, with the result that the length of the leg of a patient can be taken into account, the bearing shaft 43 of the first lever 32 may be mounted on the spindle nut of the vertically oriented linear drive 29 already mentioned (FIG. 2).

In the upper region of FIG. 2, active parts of a third measuring device 60, too, are illustrated, which is intended and designed for measuring the pressure in the region cC at the middle of the calf. This measuring device 60 also comprises, inter alia, a lever mechanism 61 which has a first lever 62. This lever 62 extends essentially vertically. The lower end 63 of this first lever 62 is mounted pivotably. Expediently, this end 63 of the first lever 62 is mounted pivotably by means of a shaft 53. The upper end 64 of the first lever 62 is assigned an elongate molding 48. The upper end 46 of this molding 48 is assigned slideably to the rod 21. The lower end 47 of the molding 48 is mounted pivotably on the upper end 64 of the first lever 62 via a joint 65. The molding 48 is designed such that its side facing away from the pressure sensors 51 has a surface which resembles the surface at the rear side of a calf.

This third lever mechanism 61 has, furthermore, a second lever 66 which likewise extends essentially vertically. This second lever 66 crosses the first lever 62. These levers 62 and 66 are connected pivotably to one another in the region of their crossing point with the aid of an axis 67. These levers 62 and 66 assigned to one another in this way thus form a third scissor mechanism. The upper end 68 of the second lever 66 of this scissor mechanism 61 is supported slideably. The lower end 69 of the second lever 66 is connected to the spindle nut 54 of a third spindle drive 55 for the value cC. This spindle drive 55 is oriented horizontally and is attached approximately where the lower end 63 of the first lever 62 is mounted pivotably by means of the shaft 53.

The spindle drive 55 is arranged and designed such that it can move the lower ends 63 and 99 of the levers 62 and 66 of the third scissor mechanism 61 toward one another and away from one another. The distance between the upper ends 64 and 68 of the levers 62 and 66 is reduced or increased correspondingly. When the distance between the upper ends 64 and 68 of the levers 62 and 66 is increased, the upper end 64 of the first lever 62 moves to the right. Since the lower end 47 of the molding 48 is connected to the upper end 64 of the first lever 62, the lower end 47 of the molding 48 likewise moves to the right, with the result that the distance between the rear surface on the molding 48 and the pressure sensors 51 lying at the same level is increased. Different sizes of the circumference of the leg in the region cC of the calf can thereby be set in the present apparatus.

So that the position of the measurement region LC can be changed in a vertical direction, with the result that the length of the leg of a patient can be taken into account, the bearing shaft 63 of the first lever 62 is attached to a second vertically oriented linear bearing 49.

FIG. 2 also illustrates a fourth measuring device 70, by means of which the dimensions in the region of a human thigh can be set and by means of which the measurements of pressure between the regions cD and cG (FIG. 1) can be carried out. This measuring device 70 also comprises, inter alia, a second elongate molding 88. That surface 89 of the molding 88 which faces away from the pressure sensors 51 has a profile which corresponds to the profile of the surface of the rear side of the thigh. The lower end 87 of this molding 88 is connected to the nut of a further horizontally oriented spindle drive 84 which makes it possible to set the value cG (FIG. 1) in the upper region LG of the thigh.

This measuring device 70 comprises, furthermore, a fourth lever mechanism 71 which has a first lever 72. This lever 72 extends essentially vertically. The lower end 73 of this first lever 72 is mounted pivotably. Expediently, this end 73 of the first lever 72 is mounted pivotably by means of a shaft 85. The upper end 86 of the second elongate molding 88 is assigned pivotably to the upper end 74 of the first lever 72.

This fourth lever mechanism 71 has, furthermore, a second lever 76 which likewise extends essentially vertically. This second lever 76 crosses the first lever 72. These levers 72 and 76 are connected pivotably to one another in the region of their crossing point with the aid of an axis 77. These levers 72 and 76 assigned to one another in this way thus form a fourth scissor mechanism. The upper end 78 of the second lever 76 of this scissor mechanism 71 is supported slideably. The lower end 79 of the second lever 76 is connected to the spindle nut of a further spindle drive 95 for setting the value cD. This spindle drive 95 is oriented horizontally and is attached approximately where the lower end 73 of the first lever 72 is mounted pivotably by means of the shaft 85.

The spindle drive 95 is arranged and designed such that it can move the lower ends 73 and 79 of the levers 72 and 76 of this scissor mechanism 71 toward one another and away from one another. The distance between the upper ends 74 and 78 of the levers 72 and 76 is correspondingly reduced or increased. When the distance between the upper ends 74 and 78 of the levers 72 and 76 is increased, the upper end 74 of the first lever 72 moves to the right. The upper end 86 of the molding 88 is connected to the upper end 74 of the first lever 72. The upper end 86 of the molding 88 therefore likewise moves to the right, with the result that the distance between the rear surface on the molding 88 and the pressure sensors 51 lying at the same level is increased. In this way, different sizes of the circumference of the leg in the lower region LD of the thigh can be set in the present apparatus.

So that the position LG of the measurement regions cG and cD can be changed in a vertical direction, with the result that the length of the leg of a patient can be taken into account, the bearing shaft 85 of the first lever 72 and the spindle drive 84 are attached to a further vertically oriented linear bearing 99.

The levers of all the scissor mechanisms may be designed as flat iron bars; so that the respective scissor mechanism has a very flat form. A plurality of scissor mechanisms assigned, flat, to one another consequently occupy only a small volume, so that even a larger number of such scissor mechanisms can be accommodated inside a leg garment 80.

FIG. 4 shows a merely diagrammatic horizontal section A-A through a further version of the present invention which corresponds to the apparatus according to FIG. 2. The apparatus according to FIG. 4 has the elongate and vertically running carrier 90 for the pressure sensors 51. This carrier 90 precedes the lever mechanisms 10 described above. The upper end part of this carrier 90 may have the abovementioned bend 8 (FIG. 2) which simulates the tip of a foot. The cross section of this carrier 90 is arcuate, the central angle of this arc expediently being 180 degrees. Such a carrier 90 has two flanks 93 and 94 with two vertically extending edge parts 91 and 92. This carrier 90 simulates the region of the shin for the leg garment in the present apparatus.

The curved face 89 on the molding or stay 88 which is illustrated in FIG. 4, by contrast, simulates the rear surface of the thigh in the present apparatus. In this embodiment of the present apparatus, two groups 50 of pressure sensors 51 are provided, the pressure sensors 51 within the respective group forming a row running virtually vertically. In each case one of these rows 50 of pressure sensors 51 is assigned to the outside of one of the flanks 93 or 94 or to the outside of one of the edge parts 91 or 92 of the carrier 90. The carrier 90, together with the sensor rows 50, and the molding 88 are surrounded by the leg garment 80. Between the vertical edges 91 and 92 of the carrier 90 and the vertical edges 78 and 79 of the molding 88 extend both portions 81 and 82 of the leg garment 80 slipped over this apparatus which are free-standing between them.

The front portions of said lever mechanisms 11, 31, 61 and 71 lie between the flanks 93 and 94 of the carrier 90 having the arcuate cross section. It is also evident from the section illustrated in FIG. 4 that this version of the present apparatus has two arrangements 101 and 102, each of which have the lever mechanisms 11, 31, 61 and 71 described above. Each of these arrangements 101 and 102 is essentially flat because the levers of the lever mechanisms 11, 31, 61 and 71 consist of flat iron bars. Such flat arrangements 101 and 102 run vertically and are located at a horizontal distance from one another, so that they are arranged parallel to one another. The stays or moldings 21, 28, 48 and 88 extend between the arrangements 101 and 102. The pivot shafts described above are common to both arrangements 101 and 102. This situation is illustrated in FIG. 4, for example, by the pivot shaft 85 which extends between the lower ends 73 of the first levers 72 of the fourth lever device 70 of the vertically running arrangements 101 and 102 arranged next to one another.

The lower ends 79 of the second levers 76 of the fourth lever device 70, which are connected to a common spindle drive 95 (not illustrated in FIG. 4), are also evident from FIG. 4. The remaining spindle drives 25, 45 and 55 and the linear bearings 29, 49 and 99, which were described above with regard to FIG. 2 and 3, may also be common to both arrangements 101 and 102. In this instance, the spindle drives 25, 45 and 55 and the linear bearings 29, 49 and 99 are located between the arrangements 101 and 102, and the respective levers of the arrangements 101 and 102 are coupled to the mutually opposite sides of the spindle drives 25, 45 and 55 and of the linear bearings 29, 49 and 99. The version of the present apparatus, as shown in FIG. 4, manages without the main support 2 (FIGS. 2 and 3). This is because the arrangements 101 and 102 standing next to one another in parallel and coupled horizontally to one another constitute a self-supporting structure. Those ends of the levers which are supported on the main support 2 in the apparatus illustrated in FIGS. 2 and 3 are supported on other levers of the respective arrangement 101 or 102, specifically, for example, as is the case with regard to the end 38 of the lever 36 in FIG. 2 or 3.

When a manufactured leg garment 80, for example a stocking or the like, is to be measured this is slipped from above over the present apparatus so that the extension 8 lies inside the tip of the stocking and the extension 15 at the upper end 14 of the first lever 12 lies inside the heel of the stocking. The shank of the stocking is then drawn further over the remaining components of the present apparatus. The leg garment 80 then lies, at the front, on the surface 6 of the carrier 90 having the pressure sensors 50 and, at the rear, on the surface 89 of the lower molding 88 and, under some circumstances, also on the surfaces of the remaining moldings or stays. In apparatuses of the prior art, leg garments were measured in a laid-flat state, which was not appropriate for the situation in which the leg garment is worn. The leg garment 80 is tested by means of the present apparatus in the open state, that is to say in the same state as if the leg garment were put on a leg. The leg garment 80 to be tested in this case surrounds the outer faces both of the carrier 90 and of the stays, and the inside of the leg garment exerts pressure on the pressure sensors 51. The pressure is advantageously measured by the sensors 50 arranged on the flanks 93 and 94 of the carrier 90, thus contributing to a more exact detection of the amount of pressure at those levels or regions LB, LB1, LC, LF, LG, etc. of the leg garment 80 which are arranged vertically one above the other.

The action c of the leg garment 8, on the levels LB, LB1, LC, LF, LG, etc. can be measured in that, first, specific distances are set between the carrier 90 and the active mechanical parts, lying opposite the carrier 90, of the individual tension devices 10, 30, 60 and 70, after a leg garment 80 has been drawn onto this apparatus. Said distances correspond to values which equate to those values which were determined during the measurement of the patient's leg at said levels LB, LB1, LC, LF, LG, etc. Thereafter, the pressure values of those pressure sensors 51 or pressure sensor groups which lie at the individual levels LB, LB1, LC, LF, LG, etc. are read off. If the read-off pressure values are such that they allow the desired healthy action and at the same time also make it possible to wear the leg garment 80 comfortably, then the leg garment has been manufactured according to the stipulations.

So that the procedure during the measurement of leg garments is efficient, it is expedient that not only the spindles of the horizontally acting spindle drives, but also the spindles of the vertically acting linear bearings are driven by electric motors, for example by stepping motors. These motors are activated from the evaluation device in such a way that the distances between the pressure sensors 51 and those active members of the respective measuring device for the respective region of the leg garment which lie opposite the respective level LB, LB1, LC, LF, LG, etc. are set quickly and exactly. Pressure values which are delivered by the pressure sensors 51 lying at said levels LB, LB1, LC, LF, LG, etc. are compared with the stipulations applying to the respective level LB, LB1, LC, LF, LG, etc. of the patient's leg. The quality of the manufactured leg garment is inferred from the result of this comparison.

The determination of the pressure value at the respective level LB, LB1, LC, LF, LG, etc. is based on the fact that the pressure sensors 51 or the groups of pressure sensors 51 of the pressure measuring devices 50 are connected individually to the evaluation device. To determine the amount of pressure at the levels LB, LB1, LC, LF, LG, etc. determined during the measurement of the patient's leg, those pressure sensors 51 or groups of pressure sensors which lie at the levels LB, LB1, LC, LF, LG, etc. are interrogated by the evaluation device. The sought pressure values can thus be detected quickly, exactly and without additional mechanical means. To carry out such an evaluation of finished products, use may be made of a computer program which, on the basis of the stipulations determined during the measurement of a patient's leg, automatically sets the distances between the pressure sensors 51 and those stays in the respective measuring device for the respective region of the leg which lie at the respective level LB, LB1, LC, LF, LG, etc., subsequently automatically reads off the pressure values at the respective level LB, LB1, LC, LF, LG, etc. and then evaluates these.

FIG. 5 shows yet another embodiment of the present apparatus, the illustration of which corresponds largely to the illustration in FIG. 2. FIG. 6 shows a top view of the embodiment of the present apparatus, as illustrated in FIG. 5, after the components of the present apparatus which are not essential for this embodiment have been omitted for the sake of greater clarity.

In that region of the main support 2 (FIG. 5) of the present apparatus where the open end part of the leg garment, mainly of a stocking, is located during the measurement of the latter, a holding device 110 for this end part of the leg garment is arranged. This region is located above the lower end of the carrier 3, which lower end can be inserted in the baseplate 1. The holding device 110 comprises a stirrup 111, to which the edge of the open end part of the leg garment can be connected. This stirrup 111 lies in a horizontal plane and is U-shaped.

The stirrup 111 has two legs 112 and 113 running parallel to one another. The first ends of these legs 112 and 113 are connected to one another by means of a web 114 to form said U-shape. In the instance illustrated, the web 114 is arcuate. A connection plate 115, which likewise lies at least essentially in said horizontal plane, is fastened at one end to the outside of this web 114. In the instance illustrated, this connection plate 115 is L-shaped, so that it has two legs 116 and 117. The free end part of one of the L-legs 117 of the connection plate 115 is connected to the web 114 of the stirrup 111.

The holding device 110 comprises, furthermore, a mechanism 120 which makes it possible to adjust the position of the stirrup 111 with respect to the carrier 3 in the horizontal direction. The adjustment mechanism 120 comprises two vertically running rods 121 and 122 which are virtually parallel to one another and which are assigned to one another such that one of the rods can slide along the other rod. In the instance illustrated, these rods 121 and 122 have a square cross section, and they are assigned to one another via one of their side faces. Means 123 are provided, with the aid of which the set position of one of the rods with respect to the other rod can be secured. These means 123 may comprise, for example, a screw and a nut. The bolt of the screw passes through the two rods 121 and 122. The position of the rods 121 and 122 in relation to one another can be secured by the tightening of a nut at the other end of the screw bolt.

So that the rods 121 and 122 can move only parallel to one another, in the instance illustrated a longitudinal groove 124 is formed in that side face of one of the rods 121 which is assigned to the other rod 122. The corresponding side face of this other rod 122 is provided with a projecting comb 125 which projects from this sidewall of the rod 122 and which is mounted longitudinally displaceably in the groove 124.

The lower end part of the first or lower rod 121 is fastened on or in the baseplate 1. The stirrup 111 is connected to the upper end part of the second or upper rod 122. For this purpose, the free end part of the second L-leg 116 of the connection plate 115 on the stirrup 111 is connected to the upper end of the second rod 122. Screw holes are formed in the end face of this end of the second rod 122. Orifices 126 corresponding to the screw holes are formed in the free end part of the second L-leg 116 of the connection plate 115. By means of screws (not illustrated) which pass through these orifices 126, the free end part of the second L-leg 116 can be fastened to the end face of the second rod.

In this embodiment of the present apparatus, two sensor devices 50 are provided, the pressure sensors 51 within the respective group forming a row running virtually vertically. In each case one of these sensor rows 50 is assigned to one of the flanks 93 or 94 of the carrier 3 having the arcuate cross section. The active faces of the sensors 51 of these rows 50 are located on the outside of the respective flank 93 or 94 of the carrier 3. The carrier 3, together with the sensor rows 50, is surrounded by the leg garment 80, only the front portion of the latter being indicated in FIG. 6.

The invention claimed is:

1. An apparatus for testing an elastic textile leg garment, the apparatus comprising:
   pressure-measuring devices (10, 30, 60, 70) which are disposed inside the leg garment during testing of the elastic textile leg garment, and wherein active elements of the pressure-measuring devices are distributed along the leg garment to be tested, the pressure-measuring device (10, 30, 60, 70) having at least one pressure sensor (51), one lever mechanism (11, 31, 61, 71) and one stay (21, 28, 48, 88), and wherein the at least one pressure sensor (51) is arranged on one side of the lever mechanism (11, 31, 61, 71) and the stay (21, 28, 48, 88) is arranged on the opposite side of the lever mechanism (11, 31, 61, 71), and wherein the at least one pressure sensor (51) and the stay (21, 28, 48, 88) lying opposite this constitute the active elements of one of the measuring devices (10, 30, 60, 70); and
   wherein the lever mechanism (11, 31, 61, 71) has a first lever (12) and a second lever (16) which cross one another and are connected pivotably to one another in the region of their crossing point by means of a pivot shaft (17), so that these levers (12, 16) constitute a scissor mechanism, wherein in each case one of the ends (13, 18) lying on both sides of the pivot shaft (17) is supported, wherein the second of the ends (14), lying on one side of the pivot shaft (17), of one of the levers (12) is intended and designed for adjusting the stays (21, 28, 48, 88), and wherein the second of the ends (19), lying on the opposite side of the pivot shaft (17), of the other lever (16) is connected to a horizontally acting adjustment device (25), with the aid of which the distance between the opposite ends (14, 18) of the levers (12, 16) can he changed.

2. The apparatus as claimed in patent claim 1, wherein a rod (21) is connected by means of a joint (22) to that side of the upper leg (20) of the first lever (12) of the first lever mechanism (11) which faces away from the pressure sensors (51), and wherein this rod (21) is coupled to the upper leg (34) of a second scissor mechanism (31) in such a way that the inclination alpha of the rod (21) with respect to a horizontal can be adjusted by means of said leg (34) of the second scissor mechanism (31).

3. The apparatus as claimed in patent claim 2, wherein a first elongate molding (48) is provided, which simulates the calf, wherein the lower end of this molding (48) is assigned to the upper end (64) of the first lever (62) of a third lever mechanism (61) by means of a joint (65), wherein the upper end region (46) of this molding (48) is assigned slideably to the rod (21), and wherein that side of the molding (48) which faces away from the pressure sensors (51) has a surface which resembles the surface of the rear side of a calf.

4. The apparatus as claimed in patent claim 2, wherein a second elongate molding (88) is provided, wherein that surface (89) of this molding (88) which faces away from the pressure sensors (51) has a profile which corresponds to the profile of the surface of the rear side of the thigh, wherein the lower end (87) of this molding (88) is connected to the nut of a horizontally oriented spindle drive (84), and wherein the upper end (86) of the molding (88) is assigned to the upper end (74) of the first lever (72) of a fourth scissor mechanism (70) by means of a joint.

5. The apparatus as claimed in patent claim 1, wherein the lever mechanisms (11, 31, 61, 71) are connected to vertically acting adjustment devices (29, 49, 99).

6. An apparatus for testing an elastic textile leg garment, the apparatus comprising:
   pressure-measuring devices (10, 30, 60, 70) which are disposed inside the leg garment during testing of the elastic textile leg garment, and wherein active elements of the pressure-measuring devices are distributed along the leg garment to be tested, and in a region of the apparatus where an open end part of the leg garment (80) is located, a holding device (110) for this end part of the leg garment (80) is disposed, the holding device (110) having a stirrup (111) running substantially horizontally, the stirrup is adapted such that the edge of the open end part of the leg garment (80) is connectable to the stirrup, and the stirrup (111) is attached to an adjustment mechanism (120) designed such that the position of the stirrup (111) with respect to the rail (3) of the apparatus can be adjusted in the vertical direction; and
   the stirrup (111) is approximately U-shaped, wherein a rail (3) and the measuring devices (10) are located between legs (112,113) of this U-stirrup, and wherein the stirrup (111) is connected to the adjustment mechanism (120) via a web (114) which extends between the first ends of the stirrup legs (112, 113).

7. The apparatus as claimed in patent claim 6, wherein the adjustment mechanism (120) comprises two rods (121, 122) which run virtually parallel to one another and which are assigned to one another such that one of the rods can slide along the other rod, and wherein means (123) are provided which make it possible to secure the set position of one of the rods with respect to the other rod.

8. An apparatus for the testing of elastic textile leg garments, in particular of stockings or tights, medical compression stockings and support stockings, the apparatus comprising pressure-measuring devices (10, 30, 60, 70); wherein the respective pressure-measuring device (10, 30, 60, 70) comprises at least one pressure sensor (51), one lever mechanism (11, 31, 61, 71) and one stay (21, 28, 48, 88); wherein the lever mechanism (11, 31, 61, 71) has a first lever (12) and a second lever (16) which cross one another and are connected pivotally to one another in the region of their crossing point by means of a pivot shaft (17), so that these levers (12, 16) constitute a scissor mechanism; wherein an end (18) of the second lever (16) which is lying above said pivot shaft (17) is supported; wherein an end (14) of the first lever (12) which is lying above said pivot shaft (17) is designed for adjusting the stay (21, 28, 48, 88), wherein the ends (13,19) of the both levers (12,16) which are lying underneath of the pivot shaft (17) are connected to a horizontally acting adjustment device (25), with the aid of which the distance between the opposite or upper ends (14, 18) of the levers (12, 16) can be changed; and wherein said lower ends (13,19) of the scissor mechanisms (11, 31, 61, 71) are connected to a vertically acting adjustment device (29,49,99) by means of which the position of the scissor mechanism can be changed in the vertical direction.

* * * * *